United States Patent
Jameel

[11] Patent Number: 5,843,126
[45] Date of Patent: Dec. 1, 1998

[54] MULTIPLE SURGICAL SUTURE APPLICATION

[76] Inventor: Irfan M. Jameel, 248 Rue Domagaya, Gaspe Quebec, Canada, G0C 1R0

[21] Appl. No.: 912,168

[22] Filed: Aug. 15, 1997

[51] Int. Cl.⁶ .................................................. A61B 17/04
[52] U.S. Cl. ........................ 606/220; 606/139; 606/144; 606/148; 606/218
[58] Field of Search ..................................... 606/215–220

[56] References Cited

U.S. PATENT DOCUMENTS

| | | |
|---|---|---|
| 19,747 | 3/1858 | Boardman . |
| 262,635 | 8/1882 | Adams . |
| 356,202 | 1/1887 | Kempshall . |
| 1,678,361 | 7/1928 | Shearon . |
| 2,058,020 | 10/1936 | Jaffe ............................................ 24/90 |
| 2,213,830 | 9/1940 | Anastasi ................................... 128/340 |
| 2,738,789 | 3/1956 | Foxworthy .............................. 128/167 |
| 2,738,790 | 3/1956 | Todt ......................................... 128/334 |
| 3,139,089 | 6/1964 | Schwerin ................................. 128/340 |
| 3,515,194 | 6/1970 | Hirst .......................................... 151/41 |
| 4,060,089 | 11/1977 | Noiles ...................................... 128/325 |
| 4,454,875 | 6/1984 | Pratt et al. ................................. 128/92 |
| 4,534,350 | 8/1985 | Golden et al. .......................... 128/334 |
| 4,610,250 | 9/1986 | Green ...................................... 128/334 |
| 4,946,458 | 8/1990 | Harms et al. .............................. 606/61 |
| 4,957,498 | 9/1990 | Caspari et al. .......................... 605/146 |
| 5,015,250 | 5/1991 | Foster ...................................... 606/147 |
| 5,222,977 | 6/1993 | Esser ....................................... 606/223 |
| 5,224,948 | 7/1993 | Abe et al. ............................... 606/147 |
| 5,258,011 | 11/1993 | Drews ..................................... 606/220 |
| 5,281,237 | 1/1994 | Gimpelson ............................. 606/144 |
| 5,374,275 | 12/1994 | Bradley et al. ......................... 606/144 |
| 5,417,701 | 5/1995 | Holmes ................................... 606/148 |
| 5,501,691 | 3/1996 | Goldrath ................................. 606/148 |
| 5,522,820 | 6/1996 | Caspari et al. ......................... 606/148 |
| 5,584,856 | 12/1996 | Jameel et al. ........................... 606/220 |

OTHER PUBLICATIONS

Laparoscopic Suturing and Tissue Approximation by Zoltan Szabo, Ch. 19.

*Primary Examiner*—Gary Jackson
*Attorney, Agent, or Firm*—Kennedy, Davis & Kennedy

[57] ABSTRACT

A multiple surgical suturing apparatus (10) is provided having a fastener member (11) and a retainer member (12). The fastener member has a series of prongs (14) removably mounted to the tubular head by a locking pin (15). Each prong has a recess 29 upon which is mounted suturing tie L joined to each other by an elongated suture S. The prongs and ties are passed through tissue to be stitched and tied off to form a series of stitches.

17 Claims, 4 Drawing Sheets

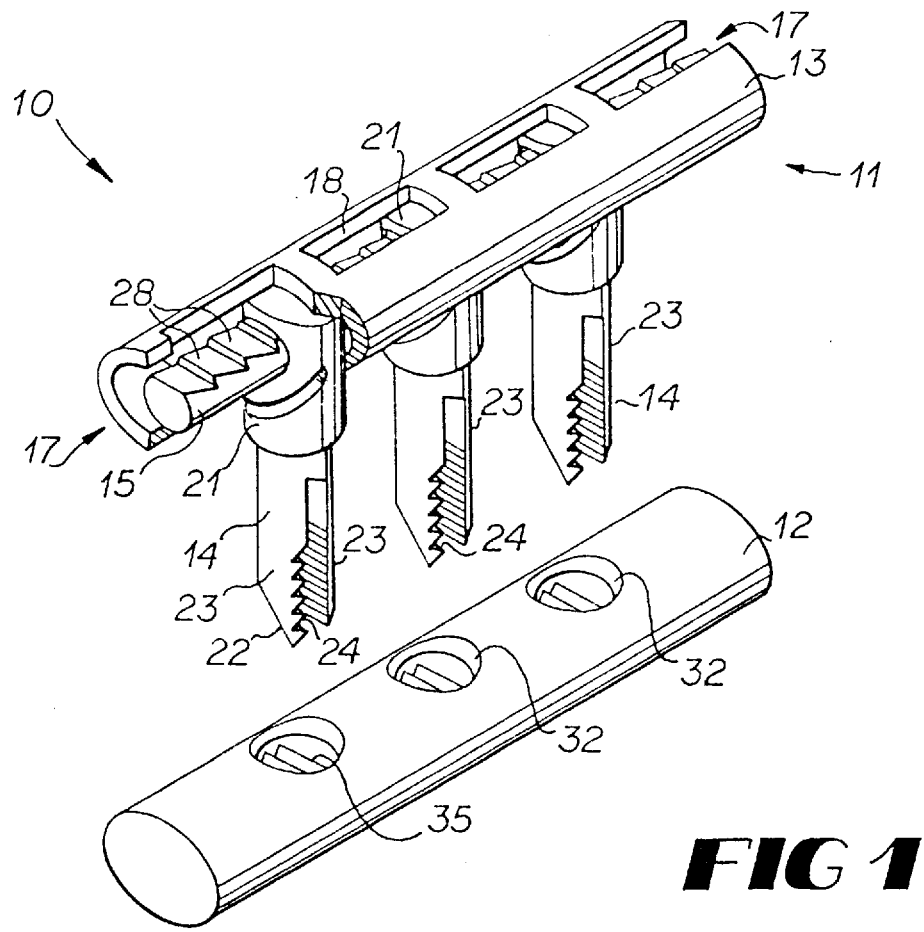
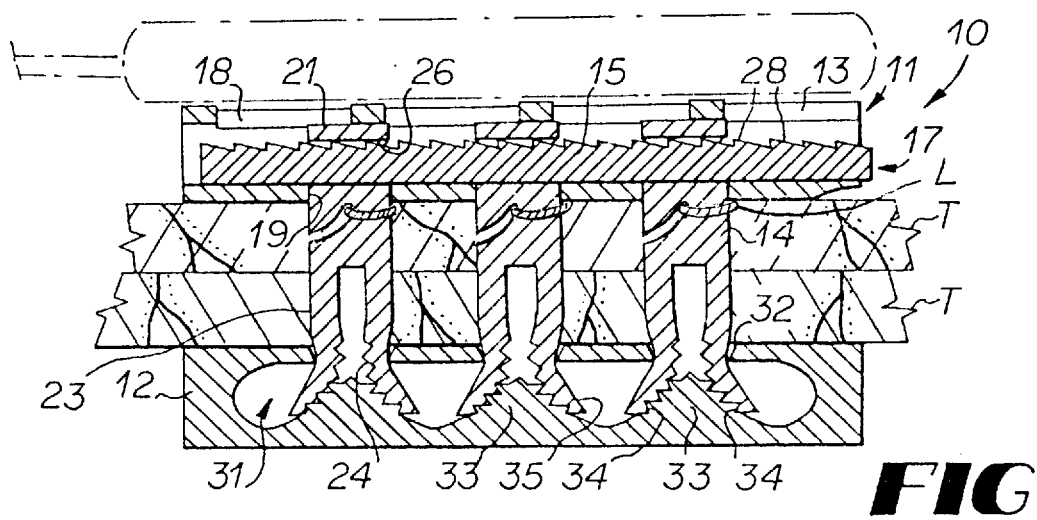

MULTIPLE SURGICAL SUTURE APPLICATION

TECHNICAL FIELD

This invention relates to surgical sutures used to stitch in vivo tissue, and especially to a method and applicator for applying multiple sutures simultaneously.

BACKGROUND OF THE INVENTION

Surgical sutures allow a surgeon to hold together body tissue. Sutures may be applied singularly or in a series depending upon the length of tissue to be held together. These sutures may be removed after a length of time or absorbed into the body. However, in order to apply multiple sutures to hold two or more fragments of tissue together, removable staples are often required in addition to sutures.

Most suture applicators are designed to apply one suture at a time. In order to apply multiple sutures a temporary suture (stay suture), tissue holding forceps, or a suitable surgical clip or staple must be applied to the tissue to hold the tissue together. The tissue is then stitched with sutures and the temporary suture, clip or staple removed. This dual stitching of the tissue produces more damage to the tissue than the required sutures and is inefficient. This inefficiency may cause problems during surgery where time requirements are essential.

The two major stitching processes used today have also had distinct drawbacks. Continuous stitching involves the use of a single suture which is passed back and forth through the tissue so that a series of continuous stitches is formed. This type of stitching provides a uniform tension which aids in preventing leakage between the sutured tissue. However, as these stitches are formed from a single strand of suture material the breakage or failure of a single stitch causes all the stitches to fail. With interrupt stitching, on the other hand, each stitch is independent of the other. Each stitch is formed by passing the suture material through the tissue, tying off each suture and severing the tied suture from the remaining suture material so that a single stitch remains tied to the tissue. This individualized stitching is continued in series along the length of the treated area. This type of stitching is typically stronger than continuous stitches. Also, the failure of one stitch does not cause all the stitches to fail. However, interrupted stitching does not prevent leakage between tissues and therefore may not be used in the suturing some tissue such as blood vessels or intestines.

Accordingly, it is seen that a need remains for a method of stitching which provides leakage prevention without the possibility of all stitches failing should one stitch break, and a device for applying such. It is to the provision of such therefore that the present invention is primarily directed.

SUMMARY OF THE INVENTION

In a preferred form of the invention a multiple surgical suturing apparatus for stitching in vivo tissue of a selected thickness comprises a plurality of prongs having a size greater than the tissue selected thickness and driving means for driving the prongs through the tissue. The prongs have tissue piercing ends and suture retention means for releasably retaining suture material. The apparatus also includes a suture having an elongated base and a plurality of ties extending from the base having a length greater than the selected thickness. With this construction, the prongs are driven through the tissue thereby forcing the ties through the tissue where they may then be tied off against the opposite side of the tissue.

In another form of the invention a method of suturing in vivo tissue comprises the steps of providing a suture having a base and a plurality of ties coupled to the base at one end and having free ends opposite the one ends, passing the free ends of the plurality of sutures through tissue to be sutured, and tieing the free ends of the ties so as to bind the tissue between the base and the tied free ends.

BRIEF DESCRIPTION OF THE DRAWING

FIG. 1 is a perspective view of a multiple surgical suture applicator embodying principles of the invention is a preferred form.

FIG. 2 is a cross-sectional view of the suture applicator of FIG. 1 shown mounted to tissue.

DETAILED DESCRIPTION

Figure 3:
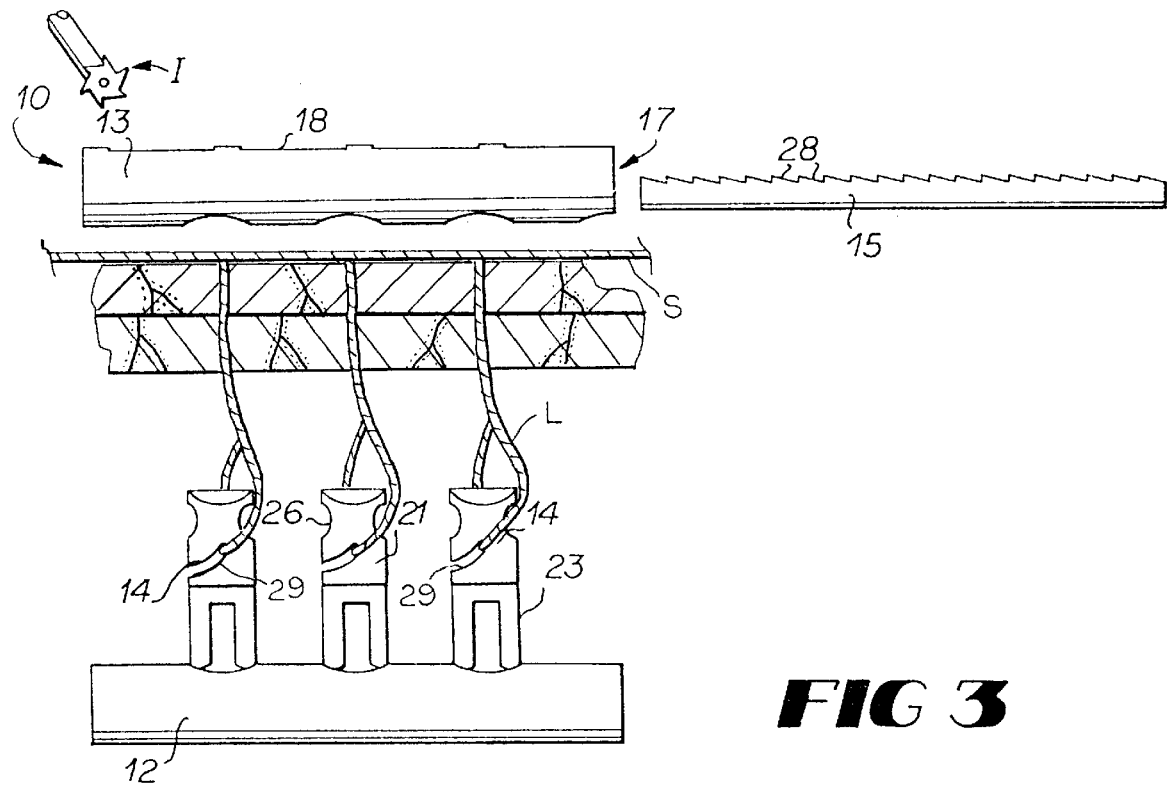
FIG. 3 is a front view of the suture applicator of FIG. 1 shown with a head portion removed from the prongs.

With reference next to the drawings, there is shown a multiple surgical suturing apparatus 10 having a fastener member 11 and a retainer member 12. The fastener member 11 has a tubular head 13, three removable prongs 14 and a removable locking pin 15 extending through the prongs 14. The tubular head 13 has open ends 17, a series of slots 18 extending into the tubular head 13 and a series of holes 19 extending into the tubular head 13 opposite the slots 18. Each prong 14 has a head portion 21 and a piercing tip 22 having two flexible arms 23 with inwardly facing serrated teeth 24. The head portions 21 of prongs 14 have a hole 26 therethrough sized and shaped to receive locking pins 15. The locking pins 15 have serrated teeth 28 extending along their entire length. The head portion 21 of the prongs 14 also have a recess 29 therein sized and shaped to releasably hold a tie or loop L of suture material. An elongated base suture S is passed through or tied to each tie L.

As best shown in FIG. 2, the retainer member 12 has an internal channel 31 and three passages 32 extending to the internal channel 31. Internal channel 31 has three inverted, V-shaped ridges 33, each aligned with a passage 32. Ridges 33 are defined by diverging slopes 34 having serrated teeth 35 thereon sized and shaped to mate with the serrated teeth 24 of the prong flexible arms 23.

In use, the fastener member 11 is positioned on one side of tissue T to be held with the prongs 14 oriented at an appropriate angle to penetrate the tissue. The retainer member 12 is held on the other side of the tissue T opposite the fastener member 11 with the retainer member passages 32 aligned with the prongs 14. The fastener member 11 and retainer member 12 are brought together thereby forcing the prongs 14 through the tissue T and into the passages 32 of the retainer member. Continued movement of the prongs 14 into the retainer member passages 32 causes the flexible arms 23 to diverge along opposite slopes 34 of ridges 33 whereby the teeth 24 of the arms interlock with the teeth 35 of the ridges, as shown in FIG. 2. The interlocking of teeth 24 and 35 locks the fastener member 11 with the retainer member 12. Relative movement between the fastener member and the retainer member is terminated when the fastener member is positioned an appropriate distance from the retainer member to hold the tissue T securely therebetween. The tissue T between the fastener member and the retainer member is ready to be sutured. As used herein, the term sutured and stitched are equivalents.

The above described method for relative movement of the fastener member in applying the suture to the tissue may be effected with a conventional instrument designed to hold the fastener member and to urge the prongs through the tissue and into the retainer member. Also, instruments which may drive the fastener member from within a blood vessel may be used so that the prongs are driven through the tissue of a blood vessel from within the blood vessel, as with an expanding mechanism such as an angioplasty balloon or laparoscopic mechanisms such as those systems employing movable guide wires, shown schematically in phantom lines in FIG. 2.

Figure 6:
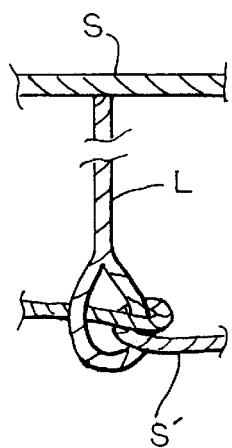
FIG. 6 is a side view, shown in partial cross-section, of the ties being tied to a second locking suture.
Figure 4:
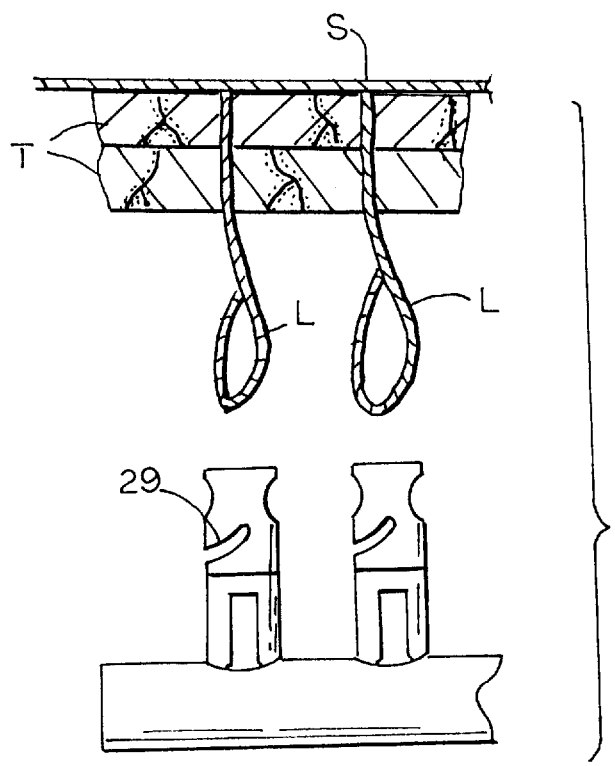
FIG. 4 is a side view, shown in partial cross-section, which shows a multiple suture having a base and a plurality of ties attached to prongs. The number of prongs correspond to the number of ties.
Figure 5:
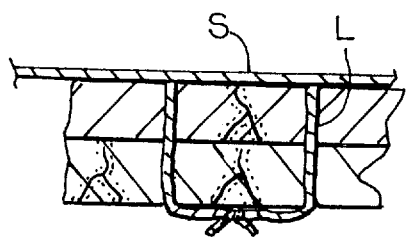
FIG. 5 is a side view, shown in partial cross-section, of multiple ties being knotted to each other.

The prongs 14 are removed by inserting an instrument I into the slot 18 of the fastener member 11 so as to contact the serrated teeth 28 of the locking pin 15. The instrument for doing such may be a motor driven wheel having teeth sized and shaped to mate with locking pin teeth 28 or simply an elongated probe, also the locking pin may be of any design which retains the prongs in place. These instruments drive the locking pin 15 from within the hole 26 of the prong head portion 21 through the open end 17 of head 13, thereby allowing the prongs 14 to be released from the tubular head 13, as shown in FIG. 3. The prongs 14 are then passed through the tissue in the same direction in which they were inserted. The passing of the prongs 14 through the tissue T forces the ties L through the tissue with the elongated base suture S remaining upon the fastener side of the tissue. As shown in FIG. 4, the ends of the ties L are then released from the prong head portion recess 29. The ends of adjacent ties are knotted to each other, as shown in FIG. 5, thereby capturing the tissue T between the knotted ends of the ties and the elongated base suture S. The tubular head 13, locking pin 15 and retainer member 12 with prongs 14 mounted thereto are removed from the body. As an alternative to knotting the adjoining ties together another elongated locking suture S' may be knotted or passed within the tie loop, to lock each tie, as shown in FIG. 6.

Figure 7:
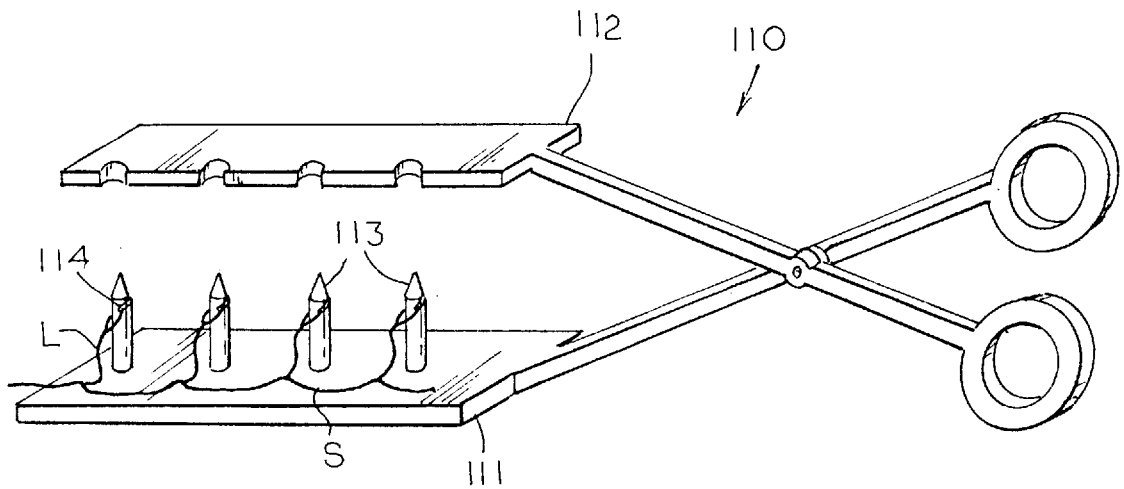
FIG. 7 is a perspective view of an apparatus for applying the multiple suture in another preferred form.

Referring next to FIG. 7, there is shown a suturing apparatus 110 having a lower arm 111 and an upper arm 112 pivotally mounted to each other for scissor like action. The lower arm 111 has four fixedly mounted prongs 113 having a recess 114 therein sized and shaped to receive the loops or ties L of a suture material. An elongated base suture S is passed through or knotted to each tie L. The upper arm 112 has four slots 116 each of which is aligned with a prong 113.

In use, the apparatus works similarly to that previously described except that subsequent to piercing the tissue the prongs 113 are backed out rather than being passed completely through the tissue. As such, the prongs are passed through the tissue, the ties L are released from the prongs, and the prongs are backed out of the tissue leaving the ties L extending through the tissue and the elongated base suture S on the entry side of the tissue. Again, the ties are then knotted to each other as shown in FIG. 5 or tied to a second base or locking suture as shown in FIG. 6.

Figure 8:
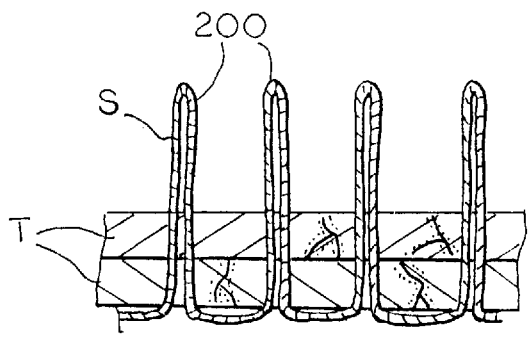
FIG. 8 is a side view of a suture embodying principles of the invention in another preferred form.
Figure 9:
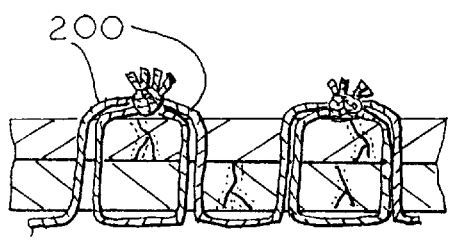
FIG. 9 is a side view of the suture of FIG. 8 shown being tied off.

With reference next to FIGS. 8 and 9, there is shown a suture S wherein portions 200 have been pulled through tissue T with the use of a previously described apparatus. The suture is of a continuous nature with each free end of portion 200 knotted to an adjacent portion 200, as shown in FIG. 9. Hence, if one suture breaks the adjacent tied pair remains intact. Conceptually, the extended portions 200 are equivalent to the previously described loops or ties, as such the extended portions should also be considered ties herein.

The just described multiple sutures incorporate the advantages of both continuous stitching and interrupted stitching while eliminating the disadvantages associated with each. The multiple suturing provides a tight, continuous pressure and uniform tension along the entire length of the stitching to minimize leakage between the adjoining tissues, similarly to continuous stitching and dissimilarly to interrupted stitching. Also, the multiple suturing provides a stitching which will not become completely undone or inoperative should a single tie become broken, similarly to interrupted stitching and dissimilarly to continuous stitching. Thus, it should be understood that the just described invention provides a uniquely uniform tension with the safety advantage of providing substantial tension should a single suture break or otherwise loosen.

It thus is seen that a simultaneous, multiple surgical sutures may now be formed which provide a uniform tension in a safe and efficient manner. It should be understood that the number of prongs and alignment may be varied according to the size and shape of the tissue to be held. As such, the apparatus may be provided with as little as two prongs. Also, the prong may be provided with any type of means for retaining suturing material, such as clips, as an alternative to the recess. Lastly, the suture ties L may be looped only at the ends thereof rather than the entire length of the looped portion or formed without a loop so long as they are capable of being releasably held by the prongs.

While this invention has been described in detail with particular references to the preferred embodiment thereof, it should be understood that many modifications, additions and deletions, in addition to those expressly recited, may be made thereto without departure from the spirit and scope of the invention as set forth in the following claims.

I claim:

1. A multiple surgical suturing apparatus for stitching in vivo tissue of a selected thickness comprising a plurality of prongs having a size greater than the tissue selected thickness, said prongs have tissue piercing ends and suture retention means for releasably retaining suture material, driving means for driving said prongs through the tissue, and a suture having an elongated base and a plurality of ties extending from said base having a length greater than the selected thickness, whereby the prongs are driven through the tissue thereby forcing the ties therethrough so as to tied against the opposite side of the tissue.

2. The suturing apparatus of claim 1 wherein said prongs are releasable from said driving means.

3. The suturing apparatus of claim 2 further comprising a retainer adapted to receive and retain said piercing end of said prongs with said prong extending through the tissue.

4. The suturing apparatus of claim 1 wherein said suture retention means comprises a recess adapted to hold said tie.

5. A surgical suturing apparatus for stitching tissue in vivo comprising a fastener having a head and a plurality of removable prongs having a shaft with a tissue piercing tip and a mounting end opposite said shaft piercing tip, a retainer adapted to be coupled to said piercing tip of said prong shafts, and a suture having an elongated base and a plurality of ties extending from said suture base and being removably mounted to said prongs, whereby the prongs pierce the tissue thereby conveying the ties through the tissue with the base upon one side of the tissue and the ties capable of being tied on the opposite side of the tissue.

6. The surgical suturing apparatus of claim 5 wherein said mounting end of said prongs have a hole therein and wherein said head comprises a tubular member adapted to receive said mounting end of said prongs and a lock pin sized and shaped to be received within said hole of said prong mounting ends mounted within said tubular member.

7. A multiple suturing apparatus for stitching tissue of a selected thickness, with said apparatus comprising:

a plurality of prongs of a selected length greater than said tissue thickness, a multiple suture having a base and a plurality of ties having a selected length greater than said tissue thickness, whereby the prongs simultaneously convey the ties through the tissue so that the base is position against one side of the tissue and the ties may be tied against the opposite side of the tissue.

8. The multiple suturing apparatus of claim 7 further comprising drive means for simultaneously driving said plurality of prongs through the tissue.

9. The multiple suturing apparatus of claim 8 wherein said prongs are releasably mounted to said driving means.

10. The multiple suturing apparatus of claim 9 further comprising a retainer adapted to receive and retain said prongs with said prong piercing the tissue.

11. A method of suturing in vivo tissue comprising the steps of:

(a) providing a suture having a base and a plurality of ties coupled to the base at one end and having free ends opposite the one ends;

(b) passing the free ends of the plurality of sutures through tissue to be sutured; and (c) tieing the free ends of the ties so as to bind the tissue between the base and the tied free ends.

12. The method of claim 11 wherein step (b) the free ends of the sutures are passed through the tissue simultaneously.

13. The method of claim 11 wherein step (c) the free ends of the ties are tied to each other.

14. The method of claim 11 wherein step (c) the free ends of the suture ties are tied to another base suture.

15. A method of suturing tissue comprising the steps of:

(a) providing a suture with a base and ties extending from the base;

(b) simultaneously passing several, spaced apart portions of the suture through the tissue so as to extend from the tissue;

(c) tieing off the suture portions extending through the tissue so as to capture the tissue.

16. The method of claim 15 wherein step (c) the suture portions are tied to each other.

17. The method of claim 15 wherein step (c) the suture portions are tied to another base suture.

* * * * *